United States Patent [19]
Ozawa et al.

[11] Patent Number: 4,618,695
[45] Date of Patent: Oct. 21, 1986

[54] METHOD OF PREPARING METHYL ESTER AND ITS HYDROCHLORIDE

[75] Inventors: Yoichi Ozawa, Yokohama; Shinichi Kishimoto, Yokkaichi; Emiko Shinohara, Saga; Tadashi Takemoto, Kawasaki; Chikahiko Eguchi, Yokohama, all of Japan

[73] Assignee: Ajinomoto Co., Inc., Tokyo, Japan

[21] Appl. No.: 611,548

[22] Filed: May 17, 1984

[30] Foreign Application Priority Data

Jun. 2, 1983 [JP] Japan ................................. 58-98716
Jun. 3, 1983 [JP] Japan ................................. 58-99038

[51] Int. Cl.$^4$ .......................................... C07C 101/02
[52] U.S. Cl. ................................. 560/41; 260/998.21
[58] Field of Search ..................... 260/112.5 R; 560/41

[56] References Cited

U.S. PATENT DOCUMENTS 3,798,207  3/1974  Ariyoshi et al. ............. 260/112.5 R

FOREIGN PATENT DOCUMENTS 0127411  5/1984  European Pat. Off. .
2152111  4/1972  Fed. Rep. of Germany .
1546979  6/1979  United Kingdom .

OTHER PUBLICATIONS

Mitsubishi, *Derwent Abst.*, No. 16297v/09, J4 8096–557, Mar. 22, 1972.
*Chemical Abstracts*, 101, 763(1984).

Primary Examiner—Delbert R. Phillips
Attorney, Agent, or Firm—Oblon, Fisher, Spivak, McClelland & Maier

[57] ABSTRACT

A method of preparing α-L-phenylalanine methyl ester and its hydrochloride, which comprises dissolving α-L-aspartyl-L-phenylalanine β-methyl ester in a methanol/hydrochloric acid mixture solvent which contains, when hydrochloric acid is expressed in terms of concentrated hydrochloric acid and water, 0 to 20% by volume of methanol, 8 to 55% by volume of concentrated hydrochloric acid and water (balance) in a concentration from 0.01 mol/dl to 0.3 mol/dl; holding the solution at 0° to 60° C. to effect intramolecular ester exchange reaction and crystallize out the formed α-L-aspartyl-L-phenylalanine methyl ester as its hydrochloride; isolating the hydrochloride; and obtaining, when required, the free ester by neutralization with an alkali, is disclosed.

4 Claims, No Drawings

METHOD OF PREPARING METHYL ESTER AND ITS HYDROCHLORIDE

DETAILED DESCRIPTION OF THE INVENTION

This invention relates to a method of preparing α-L-aspartyl-L-phenylalanine methyl ester (α-APM), which is a peptide sweetener of commercial value, and its hydrochloride.

Various methods are known for the manufacture of α-APM. In accordance with most of these methods, L-aspartic acid (L-Asp), after its amino group has previously been protected by some means, for example, with carbobenzoxy group, formyl group, a hydrogen halide or other proptective groups, is converted to its anhydride, and then the anhydride is condensed with L-phenylalanine methyl ester (PM) to form the skeleton of α-APM, followed by removal of the protective group. One of the disadvantages of these methods is a certain limitation of the yield of α-APM obtainable because the formation of the by-product β-L-aspartyl-L-phenylalanine methyl ester (β-APM) is unavoidable in the sysnthesis of α-APM from L-Asp or L-phenylalanine (L-Phe). Furthermore, there is a need for an additional step for isolating α-APM from the α- and β-APM isomeric mixture.

In the past, several methods were proposed for chemical synthesis of pure α-APM alone. For example, a Japanese Patent Application (tokkaisho No. 56-73053) teaches a method in which an NTA (N-thiocarboxy anhydride) of L-Asp is condensed with PM. However, this method also has disadvangages such as disagreeable smell of the final product, and, therefore, is not suitable for commercial production. Another Japanese Patent Application (tokkaisho No. 48-96557) discloses a method which comprises condensing the NCA (N-carboxy anhydride) derived from N-carbobenzoxy-L-aspartic acid β-benzyl ester with PM, followed by removal of the protective group through catalytic reduction to obtain α-APM, but its commercial application also seems to be difficult because of the high cost and for other reasons. Several other methods are also known for the manufacture of α-APM without forming β-APM as a by-product. Although practicable in laboratories, any of these methods has little feasibility on a commercial basis in terms of cost, availability of auxiliary materials and other factors.

The present inventors have discovered that α-L-aspartyl-L-phenylalanine β-methyl ester (methyl ester of the β-carboxyl group of the aspartic acid residue of α-L-aspartyl-L-phenylalanine) is prepared by condensing the NCA of L-Asp β-methyl ester with L-Phe. This dipeptide obtained by the above-mentioned method includes, as an inevitable consequence, no isomer having β-linkage between L-Asp and L-Phe moieties because of the synthetic route employed.

The present inventors now offer a process for preparing α-APM in high yields from this type of dipeptide obtainable, for example, by the method described above.

The present inventors have previously found that, when α-APM is allowed to stand in a mixed solvent of methanol (MeOH) and hydrochloric acid, α-APM crystallized out as its hydrochloride from the solution and, at the same time, α-L-aspartyl-L-phenylalanine β-methyl ester is formed in a small amount in the solution. It was inferred that α-L-aspartyl-L-phenylalanine β-methyl ester is formed through ester exchange reaction of α-APM. Incidentally, it was also inferred that an equilibrium is established among the compounds contained in the system.

The present inventors' further studies have revealed that α-L-aspartyl-L-phenylalanine β-methyl ester undergoes ester exchange to form α-APM followed by crystallization in the form of its hydrochloride, if α-L-aspartyl-L-phenylalanine β-methyl ester is allowed to stand under specific conditions, that is, by dissolving it in a mixed solvent of MeOH, concentrated hydrochloric acid (conc. HCl) and water consisting of 0 to 20% by volume of MeOH, 8 to 55% by volume of conc. HCl and water (balance) in a concentration ranging from 0.01 mol/dl to 0.3 mol/dl, and holding the solution at temperatures between 0° and 60° C. whereby α-L-aspartyl-L-phenylalanine β-methyl ester may be eventually converted to α-APM hydrochloride in a high yield (about 85% or higher on the basis of the starting α-L-aspartyl-L-phenylalanine β-methyl ester) by the shift of equilibrium as a result of crystallization of the hydrochloride. Incidentally, it is known that α-APM hydrochloride is very sparingly soluble (U.S. Pat. No. 3,798,207). This invention was accomplished based on these findings. No such synthesis of α-APM through ester exchange reaction has yet been disclosed.

In the method of this invention, hydrochloric acid of appropriate concentration may be used as solvent, and, if necessary, a suitable amount of MeOH may be added, so as to give a composition corresponding to 0 to 20% by volume MeOH, 8 to 55% by volume conc. HCl and water (balance), as specified above. A higher concentration of hydrochloric acid tends to lead to fission of the peptide linkage, while lower concentration results in insufficient crystallization of α-APM in the form of its hydrochloride. When MeOH content is 0% (i.e., no MeOH added), hydrolysis of the ester proceeds, while use of excess MeOH favors diesterification.

The amount of α-L-aspartyl-L-phenylalanine β-methyl ester to be dissolved in the mixed solvent of the above-specified composition must be in the range of 0.01 to 0.3 mol/dl. A lower concentration results in insufficient crystallization of α-APM hydrochloride, while a larger amount of α-L-aspartyl-L-phenylalanine β-methyl ester does not dissolve completely in the solvent.

The intramolecular ester exchange reaction must be carried out in the temperature range of 0° to 60° C. The temperature may be kept constant or may fluctuate within this range. A higher reaction temperature leads to fission of the peptide linkage, while lower temperature slows down the ester exchange reaction.

The ester exchange reaction is nearly completed in 2 to 14 days under such conditions.

At the end of the reaction, crystals of α-APM hydrochloride are separated by a suitable means, followed, when required, by neutralization to obtain free α-APM.

If appropriate amounts of MeOH, hydrochloric acid, and/or water are added to the mother liquor from which the crystals of α-APM hydrochloride have been separated so as to satisfy the above-mentioned composition conditions, followed by addition of new α-L-aspartyl-L-phenylalanine β-methyl ester, substantially all the α-L-aspartyl-L-phenylalanine β-methyl ester used as the starting material can be quantitatively converted to α-APM hydrochloride without any loss.

Crystals of α-APM can be obtained, when required, by neutralizing the α-APM hydrochloride with a suitable alkali such as sodium carbonate.

Hereinafter will be described a process of preparing α-L-aspartyl-L-phenylalanine β-Lower alkyl esters (α-AP-β-A; lower alkyl esters of the β-carboxylic acid group of the L-aspartic acid residue of the dipeptides α-L-aspartyl-L-phenylalanine, including α-L-aspartyl-L-phenylalanine β-methyl ester).

L-Aspartyl-L-phenylalanine alkyl esters are present in two isomeric forms α-APA and β-APA, depending on whether L-phenylalanine (L-Phe) alkyl esters are combined with L-aspartic acid (L-Asp) to form peptide linkage at the α-carboxyl group or at the β-carboxyl group of the latter (α-APA or β-APA).

Of these two isomeric forms, the α-isomers (α-APA) have commercial value as sweeteners, and the highest sweetness is observed when the alkyl group is methyl (α-APM). It is also known that the β-isomers taste bitter.

Many processes have been proposed for the preparation of α-APA, particularly α-APM, useful as a sweetener. Of these, most processes deemed feasible for commercial application comprise the steps of converting L-Asp, with its amino group previously protected by a suitable means, into the anhydride; condensing the protected anhydride with L-phenylalanine methyl ester (PM) to form the peptide linkage; removing the protective group to give a mixture of α-APM and β-APM (β-L-aspartyl-L-phenylalanine methyl ester); and isolating e.g., through crystallization, only α-APM from this mixture, or as in other suitable forms, such as α-APM hydrochloride.

All these methods suffer from the following unavoidable problems, such as: (1) Since these processes intrinsically give β-isomer as a by-product, β-APM or N-protected derivative thereof must be removed during the manufacturing process by means of fractional crystallization, extraction or other methods; (2) Formation of β-APM other than α-APM is unavoidable. That entails an actual limitation of the yield of α-APM obtainable; (3) Therefore, in order to obtain α-APM at low costs on a commercial basis, it is imperative to hydrolyze the separated β-APM or its related compounds to recover L-Asp and L-Phe for reuse. That results in the complicated manufacturing steps; (4) The amino group of L-Asp must be protected with expensive carbobenzoxy group (Z), formyl group or the like. Furthermore, these protective groups must be removed by reduction or use of hydrochloric acid, which requires elaborate equipment in commercial production; and (5) Since L-Phe, more expensive than L-Asp, must be converted into its methyl ester (L-Phe-OMe) for condensation reaction, its esterification yield has a substancial effect upon the yield of the final product α-APM.

To overcome these difficulties associated with the conventional chemical synthesis of α-APM, the present inventors have established a new process for the absolute synthesis of α-APM that doesn's evoke β-isomer through a key intermediate α-L-aspartyl-L-phenylalanine β-methyl ester (α-AP-β-M).

The sysnthesis of this key intermediate and the preparation of α-APM therefrom will be described below.

The N-carboxy anhydride (NCA) of L-aspartic acid β-methyl ester can be prepared, for example, by reaction of L-Asp β-methyl ester or its hydrochloric with phosgen or its dimer. L-Asp β-methyl ester or its hydrochloride, in turn, can be obtained by esterification of L-Asp with methanol (MeOH) in the presence of an acid catalyst such as $SOCl_2$ or HCl. Conversion of L-Asp β-methyl ester to its N-carboxy anhydride serves both to protect the amino group of L-Asp β-methyl ester and to activate the α-carboxyl group.

Condensation of this N-carboxy anhydride with L-Phe is carried out as follows:

As the reaction medium, water alone or a mixed solvent of water and a water-soluble organic solvent (hereinafter referred to as "aqueous solvent" collectively) must be used. Use of an organic solvent alone results in lower condensation yield because of the low solubility of L-Phe-ONa in it. High solubility of the N-carboxy anhydride can be achieved by the use of an aqueous solvent, thus causing the reaction to proceed smoothly. Suitable watersoluble organic solvents include acetonitrile, tetrahydrofuran, dioxane and acetone, but acetonitrile is the most preferable in terms of reaction yield.

The condensation reaction in accordance with this invention must be conducted under a weakly alkaline condition. An acid condition lowers the reactivity of the amino group of L-Phe and almost no condensation reaction takes place accordingly. Strongly alkaline conditions are not preferable because of the polymerization of the N-carboxy anhydride, the hydrolysis of the ester linkage and the other side reactions which are likely to occur. To avoid these troubles, the reaction should be carried out in the pH range from about 9.5 to about 11. Any basic substance that does not react with the reactants may be employed as pH regulator, but use of a weak alkali such as carbonates and bicarbonates is preferred.

Reaction temperature, amounts of reactants to be used (mole ratio) and other reaction conditions will be detailed later.

N-carboxy-α-L-aspartyl-L-phenylalanine β-methyl ester, i.e., the product of the condensation reaction, is very unstable and can be decarboxylated by simply acidifying the condensation reaction solution obtained with a suitable mineral acid, such as hydrochloric or sulfuric acid. Accordingly, there is no need for isolating the N-carboxy-α-L-aspartyl-L-phenylalanine methyl ester from the solution prior to decarboxylation.

The decarboxylated product (α-AP-β-M) may or may not be isolated from the reaction mixture before being subjected to the succeeding step (for example, intramolecular ester exchange reaction). When this compound is to be isolated, this may be accomplished, for example, by the following method; The solution obtained by condensation reaction of the NCA of L-Asp β-methyl ester with L-Phe-Ona is washed with acetonitrile to remove the unreacted NCA, the aqueous layer is acidified with a mineral acid such as diluted sulfuric acid to effect decarboxylation to form α-AP-β-M, the inorganic salt is precipitated by addition of MeOH and collected by filtration, and the filtrate is concentrated to give the aimed-at white crystals of α-AP-β-M.

α-APM may be prepared from α-L-aspartyl-L-phenylalanine β-methyl ester (α-AP-β-M), for example, by dissolving it in a MeOH/hydrochloric acid mixed solvent of proper composition and allowing the solution to stand. Intramolecular ester exchange proceeds spontaneously to give α-APM, which crystallizes out from the solution in the form of its hydrochloride. Free α-APM can be easily obtained from this hydrochloride, when required, by neutralizing it in the usual way.

The process of transforming this intermediate α-AP-β-M into α-APM has the outstanding industrial advantages as described below, compared with conventional processes. (1) Since the preparation of this intermediate logically gives only α-isomer that is not accompanied with any formation of β-linkage between L-Asp and L-Phe, there is no need for the unavoidable step of separating β-isomers (β-APM or N-protected β-APM) in conventional processes. This means significant simplification of the entire manufacturing process and higher yield of α-APM, and also eliminates the elaborate equipment for recovering L-Asp and L-Phe through hydrolysis of β-isomers. (2) Since the amino group of L-Asp β-methyl ester moiety of the condensate with L-Phe is protected with $CO_2$ (in the form of carbamic acid), the intermediate α-AP-β-M can be prepared directly from the condensate by spontaneous decarboxylation essentially without protective-group removal step. (3) In conventional processes, L-Phe must be converted to its methyl ester before being subjected to the condensation with L-Asp with its amino group protected or non-protected, and therefore the yield of α-APM is partly dictated by the yield of this esterification step. In contrast, the process of this invention eliminates this esterification step, thus achieving higher yield of α-APM based on L-Phe, which is generally a more expensive material than L-Asp. (4) More efficient utilization of MeOH because of the intramolecular ester exchange. (5) No possibility of racemization. (6) α-APM can be manufactured at a low cost because of the higher overall yield and use of inexpensive chemicals.

Method of preparing this intermediate, α-L-aspartyl-L-phenylalanine β-methyl ester (α-AP-β-M), will further be detailed below.

(a) Preparation of L-aspartic acid β-methyl ester is known (Karoly Jakus, et. al, Hung, 149,544, Aug. 31, 1962, Appl. Dec. 22, 1960).

(b) Preparation of N-carboxy anhydride of L-Asp β-methyl ester is also known (Jap. Patent Appl. Publn. tokkosho 43-20181).

(c) α-L-aspartyl-L-phenylalanine β-methyl ester can be prepared, for example, as described below.

For the condensation of the NCA of L-Asp (β-methyl ester with L-Phe, it is preferable to use each reactant in the form of a solution.

For example, 1.7 moles of L-Phe is mixed with 1 to 10 (normally 1.7) moles of a carbonate such as $Na_2CO_3$, $K_2CO_3$ or $(NH_4)_2CO_3$, or 1 to 20 (normally 3.4) moles of a bicarbonate such as $NaHCO_3$ or $KHCO_3$, 1 to 20 (normally 7) liters of water, normally 1.7 liters of 1N-NaOH, and 2 to 20 (normally 9) liters of a water-soluble organic solvent, such as acetonitrile, propionitrile, tetrahydrofuran, dioxane and acetic acid, and the mixture is cooled to −25° C. to 0° C. (normally about −10° C.). If a higher reaction temperature is used, the yield will be lowered, while a lower temperature will cause freezing, wherely stirring is made to become difficult. On the other hand, 0.85 to 3.4 moles (normally an equivalent or slightly excess amount) of purified N-carboxy anhydride of L-Asp β-methyl ester is dissolved in 1 to 10 (normally 3) liters of such a water-soluble organic solvent as mentioned above, like acetonitrile, and the solution is cooled to a temperature at which freezing should not take place, for example, −25° C. to 0° C. (normally −15° C. to −10° C.). This cooled solution of the anhydride is added to the solution of L-Phe prepared above, and the mixture is allowed to stand with mild stirring at −25° C. to 0° C. (normally about −10° C.)

Stirring is stopped after about two hours, and the separated aqueous layer is taken, washed with acetonitrile, and neutralized with a mineral acid, such as diluted sulfuric or hydrochloric acid, to effect decarboxylatin. 5 to 20 liters of MeOH is added, the sodium sulfate thus precipitated is filtered off, and the filtrate is concentrated to give crystals of α-AP-β-M. Yield: 85%.

(d) α-APM can be prepared from α-AP-β-M as described below. α-AP-β-M is dissolved, for example, in MeOH/hydrochloric acid mixed solvent consisting of 0 to 20% by volume of MeOH, 8 to 55% of conc. HCl and water (balance), the solution is allowed to stand at room temperature, ant the precipitated α-APM hydrochloride is collected.

If α-AP-β-M is newly added to the mother liquor and the composition of the solution is adjusted so as to satisfy the above-specified condition, the conversion of α-AP-β-M to α-APM will be nearly complete.

Of α-L-aspartyl-L-phenylalanine alkyl esters, only lower alkyl esters are useful as sweetener, which include, other than α-APM (methyl ester), ethyl ester, propyl ester and other homologues. Corresponding intermediates for the manufacture of these homologues, α-AP-β-A, can be prepared in a similar way as for α-AP-β-M.

The following examples illustrate the practice of this invention, but are not intended to limit its scope.

EXAMPLE 1

Preparation of L-Asp β-methyl ester hydrochloride

Thionyl chloride (124 ml) was slowly added to MeOH (830 ml) kept at −30° C., and L-Asp (160 g) was added in small portions with stirring to give a clear solution. The temperature was gradually raised to room temperature, diethyl ether (2,400 ml) was added dropwise. The amied-at L-Asp β-methyl ester was precipitated in the form of its hydrochloride, collected by filtration and washed with ether. Yield: 177 g (75%)

EXAMPLE 2

Preparation of the N-carboxy anhydride of L-Asp β-methyl ester

L-Asp β-methyl ester hydrochloride (0.1 mole) was suspended in anhydrous tetrahydrofuran (THF, 808 ml), phosgen dimer (20.2 ml) was added to this suspension, and the mixture was stirred at 20° to 30° C. (room temperature). When the mixture became clear after above five hours, the solution was concentrated at below 30° C. under reduced pressure, to give crystals of the N-carboxy anhydride. Yield: 16.4 g (95%).

In this connection, if no crystals are formed, the concentrate can be subjected to the next step after washing with an organic solvent that does not dissolve nor decompose the N-carboxy anhydride (e.g., n-hexane) to remove remaining THF, phosgen dimer, phosgen and HCl.

EXAMPLE 3

Preparation of α-AP-β-M

L-Phe (28 g, 0.17 mole) and $Na_2CO_3$ (17 g, 0.16 mole) were dissolved in water (680 ml). To this solution were added 1N-NaOH (170 ml) and acetonitrile (850 ml), and the mixture was cooled to −10° c. A solution of N-carboxy anhydride of L-Asp β-methyl ester (0.12 mole) in acetonitrile (272 ml), previously cooled to −10° C., was added with sitrring to the alkaline solution of L-Phe prepared above, the mixture was stirred at −10° C. for an additional two hours, the separated acetonitrile layer was removed, and the aqueous layer was washed with 1 liter of acetonitrile. After controlling pH to 5.0 with sulfur acid, MeOH (1.700 ml) was added to the aqueous layer, the inorganic salts were precipitated and filtered off, and the filtrate was concentrated at 40° C., whereby α-L-aspartyl-L-phenylalanine β-methyl ester was crystallized out.

The crystals were collected by filtering. Yield: 29.8 g (74.5%).

EXAMPLE 4

Preparation of α-APM hydrochloride

MeOH (1.0 ml), conc. HCl (3.4 ml) and water (5.1 ml) were mixed, 4.2 g α-L-aspartyl-L-phenylalanine β-methyl ester was dissolved in 7 ml of the mixed solvent, and the solution was held at 25° C. α-APM hydrochloric crystallized out in increasing amount with the passage of time, and 2.93 g (about 62% yield) was collected by filtration after eight days.

A similar experiment, when repeated, gave 4.16 g of the product (88% yield) after 14 days.

EXAMPLE 5

Preparation of α-APM hydrochloride

MeOH (1.3 ml), conc. HCl (3.4 ml) and water (5.1 ml) were mixed, 4.2 g of α-L-aspartyl-L-phenylalanine β-methyl ester was dissolved in 6.4 ml of the mixed solvent, and the solution was held at 25° C. As in EXAMPLE 4, α-APM hydrochloride crystallized out with the passage of time, the collected amount being 3.3 g (70% yield) after eight days.

A similar experiment, when repeated, gave 4.1 g (87%) of the product after 11 days.

EXAMPLE 6

Preparation of α-APM hydrochloride

To the mother liquor obtained in EXAMPLE 5 was added 1.2 ml conc. HCl, and 4.2 g of α-L-aspartyl-L-phenylalanine β-methyl ester was dissolved in the resulting solution thus prepared. The solution was held at 30° C.

The yield of α-APM hydrochloride obtained after eight days was 4.6 g (97% yield).

EXAMPLE 7

Preparation of α-APM hydrochloride

MeOH (1.2 ml), conc. HCl (3.0 ml) and water (5.8 ml) were mixed, 4.2 g of α-L-aspartyl-L-phenylalanine β-methyl ester was dissolved in 7 ml of this mixed solvent, and the solution was held at 40° C. for the first one day, and at 25° C. for additional five days.

The yield of α-APM hydrochloride was 3.4 g (72% yield).

EXAMPLE 8

Preparation of α-APM 4 g α-APM hydrochloride was dissolved in 100 ml water and the resultant solution was, while maintained at a lowered temperature, adjusted in the pH to 4.8 with an aqueous $Na_2CO_3$-saturated solution. The resultant neutraraized solution was kept at 5° C. overnight.

The crystals precipitated were collected by fillering and dried to give 2.65 g α-APM.

EXAMPLE 9

Preparation of α-APM hydrochloride

Water (7.0 ml) and conc. HCl (3.0 ml) were mixed, 4.2 g α-L-aspartyl-L-phenylalanine β-methyl ester was dissolved in 7 ml of this mixed solvent, and the solution was held at 25° C. for eight days.

The yield of α-APM hydrochloride was 1.28 g (27% yield).

As is evident from the foregoing, the method of this invention provides the first chemical synthetic means that can produce α-APM alone at low costs.

What is claimed is:

1. A method of preparing an α-L-aspartyl-L-phenylalanine β-lower alkyl ester comprising reacting an N-carboxy anhydride of L-aspartic acid β-lower alkyl ester with L-phenylalanine in an aqueous solvent at a pH of from about 9.5 to about 11, followed by decarboxylation of the resultant N-carboxy-α-L-aspartyl-L-phenylalanine β-lower alkyl ester by acidifying said resultant ester with a mineral acid, wherein said lower alkyl ester is a methyl ester, ethyl ester or propyl ester.

2. The method of claim 1, wherein said aqueous solvent is selected from the group consisting of water alone and a mixed aqueous solvent of water and a water-soluble organic solvent selected from the group consisting of acetonitrile, tetrahydrofuran, dioxane and acetone.

3. The method of claim 1, wherein said pH of about 9.5 to about 11 is produced by adding a sufficient amount of an alkali carbonate or bicarbonate to said aqueous solvent.

4. The method of claim 1, wherein said mineral acid is diluted sulfuric acid or hydrochloric acid.

* * * * *